United States Patent [19]

Doty

[11] Patent Number: 4,599,086
[45] Date of Patent: Jul. 8, 1986

[54] SPINE STABILIZATION DEVICE AND METHOD

[76] Inventor: James R. Doty, 614 Concerto La., Silver Spring, Md. 20901

[21] Appl. No.: 742,410

[22] Filed: Jun. 7, 1985

[51] Int. Cl.$^4$ .............................................. A61F 2/44
[52] U.S. Cl. .................................... 623/17; 128/92 R; 128/92 C; 128/92 D
[58] Field of Search ............. 128/69, 75, 92 R, 92 A, 128/92 B, 92 C, 92 D; 623/17

[56] References Cited

U.S. PATENT DOCUMENTS

| | | | |
|---|---|---|---|
| 3,406,625 | 10/1968 | Chamness et al. | 101/93.09 |
| 3,426,364 | 2/1969 | Lumb | 623/17 |
| 3,939,497 | 2/1976 | Heimke et al. | 128/92 C X |
| 4,304,011 | 12/1981 | Whelan, III | 128/92 C X |
| 4,309,777 | 1/1982 | Patil | 128/92 C X |
| 4,401,112 | 8/1983 | Rezaian | 128/92 C X |
| 4,479,491 | 10/1984 | Martin | 128/69 X |
| 4,502,160 | 3/1985 | Moore et al. | 128/92 C X |
| 4,502,161 | 3/1985 | Wall | 128/92 C X |
| 4,553,273 | 11/1985 | Wu | 128/92 B X |
| 4,554,914 | 11/1985 | Kapp et al. | 128/69 X |

Primary Examiner—Edgar S. Burr
Assistant Examiner—Moshe I. Cohen
Attorney, Agent, or Firm—Lalos, Keegan & Kaye

[57] ABSTRACT

A spinal stabilization device positionable between separated but neighboring vertebral bodies to stabilize a spinal column which has been rendered unstable by disease. The device includes a vertebral body prosthesis containing at least one pair of oppositely disposed anchoring pins which are advanced out of the prosthesis into the abutting vertebral bodies to secure the prosthesis to and between them. On its anterior side the prosthesis has an opening communicating with the pins inside the prosthesis. A wrench is inserted into the opening until it engages the pair of pins, and then the wrench is rotated to advance the pins into the abutting vertebral bodies. Detent pins bias the anchoring pins against the wrench and lock the anchoring pins in place when in their fully extended anchoring positions. Spacer members can be attached to the ends of the prosthesis thereby elongating it to accommodate separations between neighboring vertebral bodies of varying dimensions.

49 Claims, 9 Drawing Figures

FIG. 3.
FIG. 5.
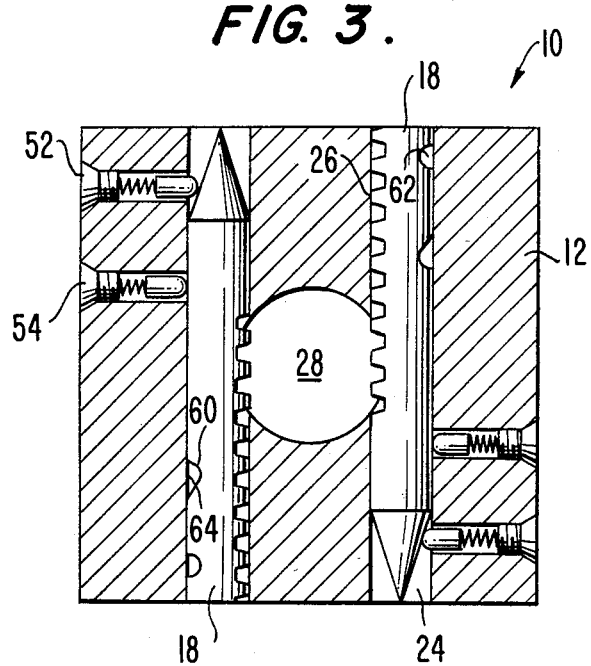
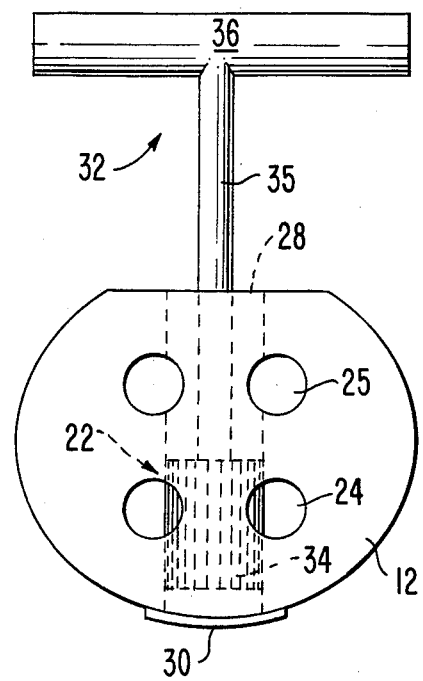
FIG. 4.
FIG. 6.
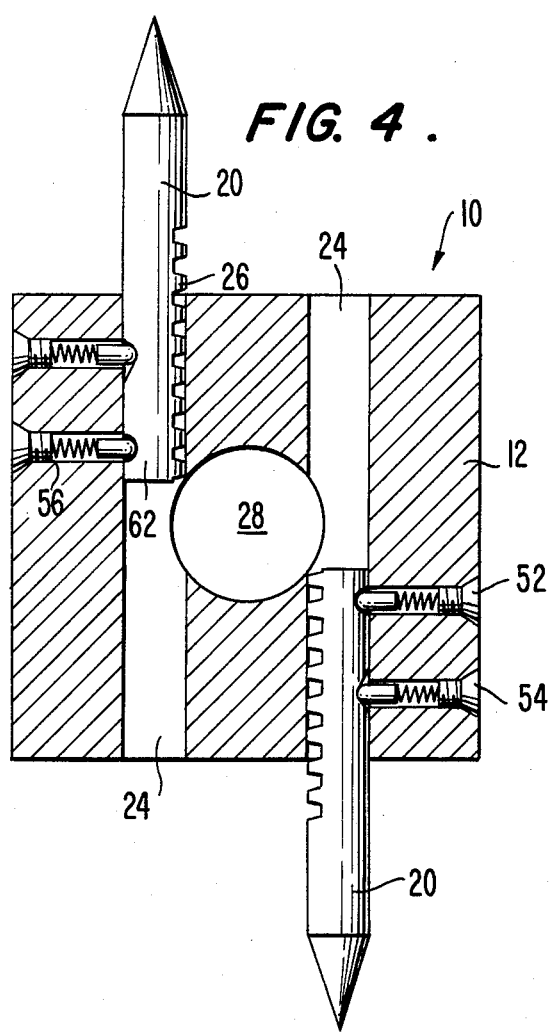
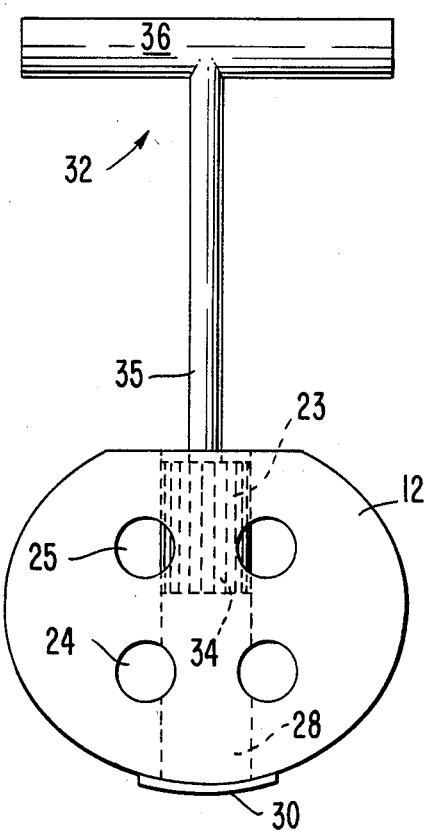

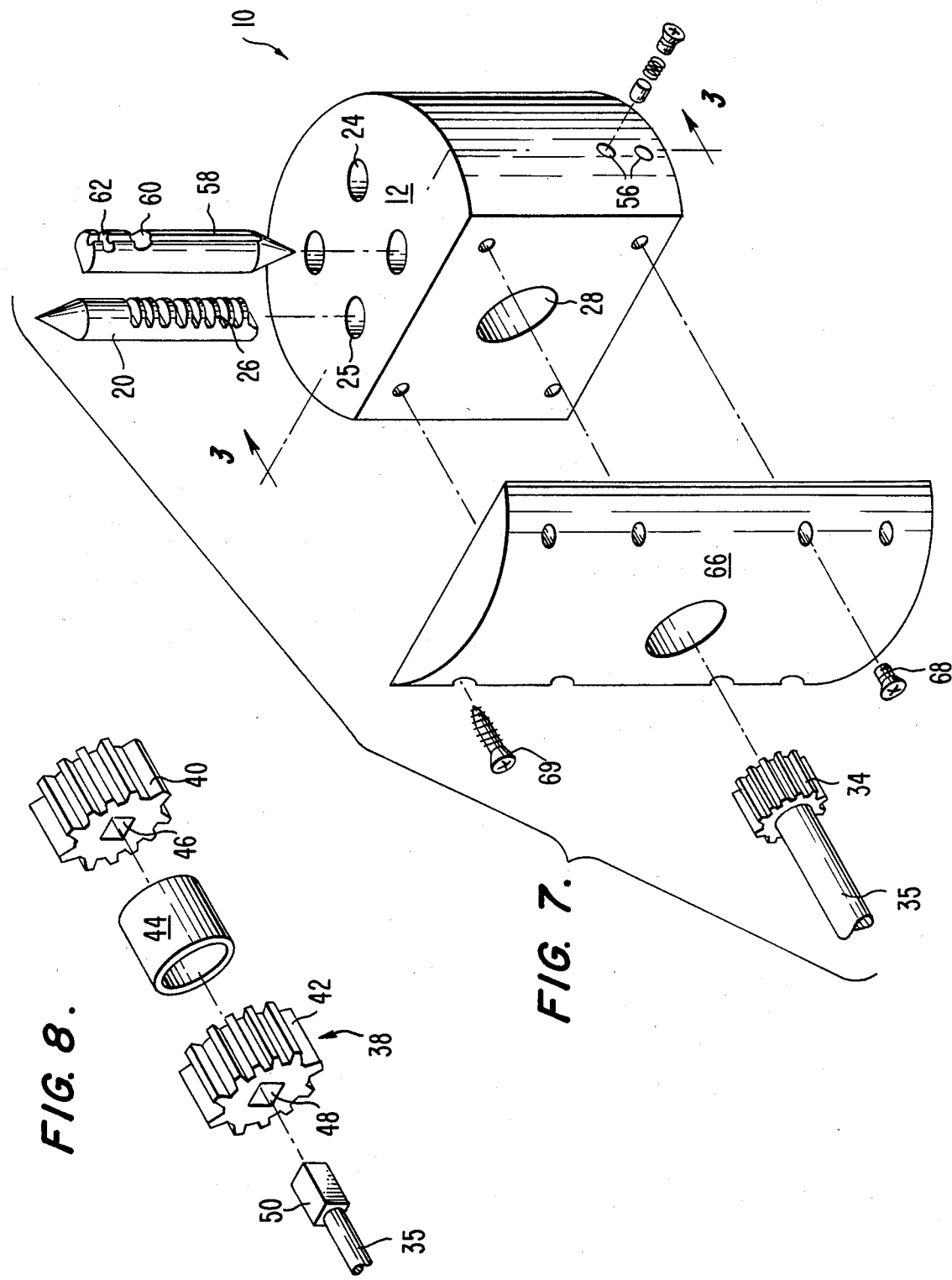

SPINE STABILIZATION DEVICE AND METHOD

BACKGROUND AND OBJECTS OF THE INVENTION

The present invention relates to devices and methods for stabilizing the spine. It more particularly relates to anterior stabilization of a spinal column (backbone) that has been rendered unstable by any disease such as a tumor, infection, or congenital anomalies affecting the vertebral bodies or associated supporting structures.

Preservation of neurologic function and relief of pain are the primary goals of treatment of diseases affecting the vertebral bodies. Oftentimes such diseases themselves destroy the vertebral body or the surgical treatment necessitates its resection. As a result of the loss of bony support, the vertebral column is unstable causing pain, progressive neurologic deterioration, and physical deformity of the back. In such cases stabilization of the spinal column by an anterior surgical approach may be required.

Each of the various procedures described in the past, however, has its individual shortcomings. No entirely satisfactory method until the present invention has been developed for effectively stabilizing the spine from the anterior surgical approach.

The most commonly used method of anterior spine stabilization is to fill the space of the resected vertebral bodies with methylmethacrylate or other similar plastic or plastic-like polymers. Difficulties encountered with this method include: (1) the inability to bond securely the plastic material to tissue or bone, (2) the potentially injurious heat released into the surrounding tissue because of the exothermic chemical reaction required for polymerization of the plastic, (3) potential stress fractures of the plastic caused by mechanical forces related to weight bearing, and (4) the need to mold the plastic to the appropriate size which is often technically cumbersome and difficult. Also, to secure the methylmethacrylate adequately, metallic pins or struts must be incorporated into the molded methylmethacrylate after their impaction or penetration into the adjacent vertebral bodies (vide infra).

Another common method of anterior spine stabilization utilizes bone to act as a replacement for the vertebral body after its removal because of disease. Bone of the iliac crest, fibula, or tissue-banked cadaver bone has been used. However, several limitations of this technique exist: (1) Immediate stabilization is not possible because adequate bony fusion requires three to six months. As a result, such individuals must wear an external spinal stabilization device for weeks or months postoperatively. Patient tolerance of such externally worn devices is often poor. (2) Oftentimes, especially when radiation therapy and/or chemotherapy are required to treat the primary disease process affecting the spine, the implanted bone graft does not survive and this results in further spinal instability secondary to resorption of the bone graft. This shortcoming has attempted to be overcome by a surgical procedure in which a bone graft on a vascularized pedicle is used since it is felt that most failures are due to inadequate blood supply to the graft. However, this procedure is technically difficult and therefore not commonly used. Even under the best of circumstances, the bone graft is partially resorbed and collapse of the vertebral space can lead to compression of the neural tissues in the spinal canal.

Attempts at spinal stabilization have also been performed utilizing a variety of metal pins and struts as mentioned previously. One common method is to penetrate adjacent vertebral bodies with Steinmann pins and then surround the pins with methylmethacrylate. Many technical problems are associated with this procedure including (1) those difficulties specially related to methylmethacrylate; (2) the inability to maintain distraction adequately while polymerization of the plastic is taking place; (3) the inability to adequately place the pins because of space restrictions; and (4) the fracture of the pins resulting in loss of stability and possible movements of the methylmethacrylate.

Another method for anterior spinal stabilization utilizes one or two metal rods attached by screws to the lateral aspect of the adjacent vertebral bodies. This procedure was first described by Dunn in 1980. There are two primary limitations of this procedure. First, it cannot be used in certain areas of the spine because of the vital structures adjacent to the lateral aspect of the vertebral body. Second, the device is inherently weak since mechanical stresses are maximally exerted at the site of attachment of the device to the vertebral body by small metal screws.

Metal rod distraction utilizing Harrington or Knodt rods, with or without methylmethacrylate, is another method to stabilize the spine via the anterior approach. This procedure was described by Harrington in 1976. One or more rods are typically attached via hooks to the anterior portion of the vertebral body and they can then be covered with methylmethacrylate to further secure them in place. The major disadvantages of this technique is the slippage of the stabilizing rods secondary to the mechanical forces generated by spine movement. These forces are greatest at the site of hook insertion and may cause fracture of the vertebral body to which it is attached. Moreover, involvement of the adjacent vertebral bodies with disease may weaken the bone at the site of hook insertion and lead to migration of the rods with resultant collapse of the spinal column.

Accordingly, the principal object of the present invention is to provide a novel device and method for stabilizing the spinal column but without the shortcomings and disadvantages of the prior methods as set forth above.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 3 is a top cross-sectional view of the device of FIG. 1 with the anchoring pins illustrated in their retracted position.

FIG. 4 is a view similar to FIG. 3 with the anchoring pins illustrated in their fully extended anchoring position.

FIG. 5 is an end cross-sectional view of the device of FIG. 1 illustrating the wrench in its posterior engaging position.

FIG. 6 is a view similar to FIG. 5 with the wrench in its anterior engaging position.

FIG. 7 is a perspective exploded view of the device of FIG. 1.

FIG. 8 is a perspective exploded view of a second embodiment of the gear mechanism illustrated in isolation of the device of FIG. 1.

DETAILED DESCRIPTION OF THE INVENTION

Figure 1:
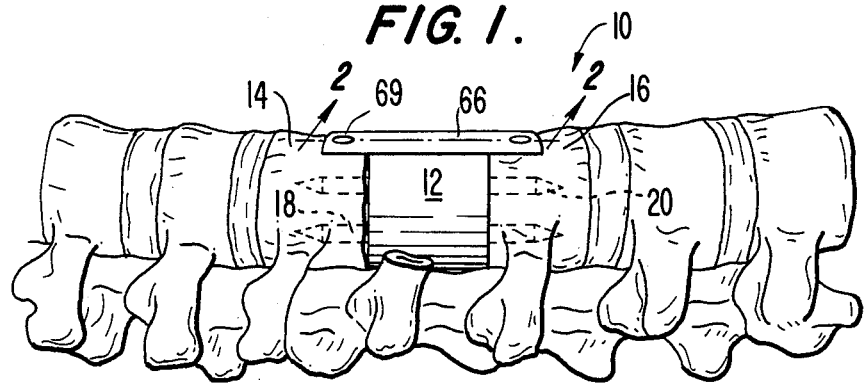
FIG. 1 is a perspective view of a spine stabilization device of the present invention shown secured to the spinal column.
Figure 2:
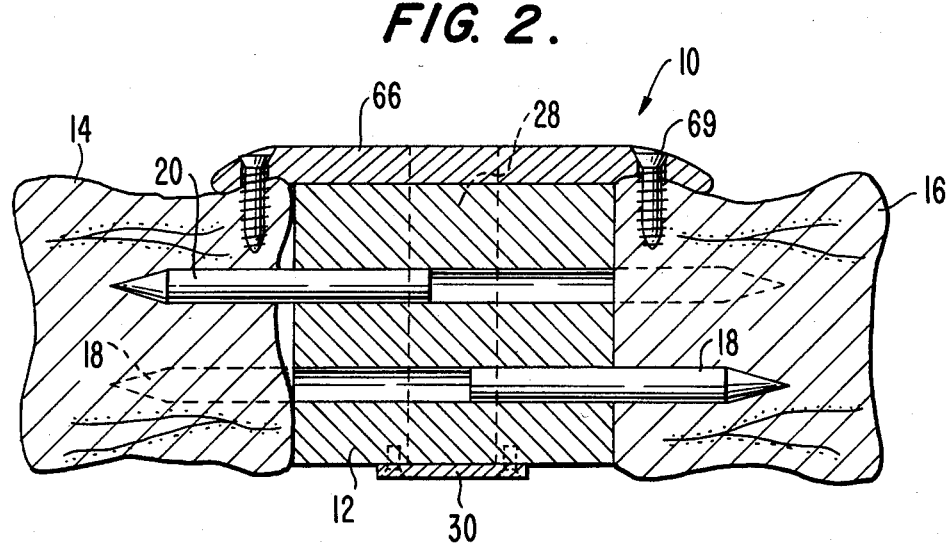
FIG. 2 is an enlarged cross-sectional view of the device of FIG. 1 taken along line 2—2.

A spine stabilization device according to the present invention is illustrated generally at 10 in FIGS. 1, 2 and 7. It is seen to be comprised of a vertebral body prosthesis 12 made of a bio-compatible material such as metal or plastic and approximating the dimensions of one human vertebral body. As will be described later, prosthesis 12 has the ability to be elongated when necessary to accommodate different dimensions between the vertebral bodies 14, 16. Contained within prosthesis 12 are two pairs of biocompatible metal anchoring pins 18, 20 which are advanced from their retracted position, as best illustrated in FIG. 3, to their fully extended position as illustrated in FIGS. 4 and 2 with their pointed ends penetrating the abutting vertebral bodies.

Neighboring, but separated vertebral bodies are first distracted as by temporarily attaching conventional distraction devices (not shown) and prosthesis 12 then anteriorly interposed between the distracted vertebral bodies. Pins 18, 20 are in their retracted position, as shown in FIG. 3, when prosthesis 12 is inserted into the separation between neighboring vertebral bodies 14, 16. After being inserted into proper anatomical position, the anchoring pins 18, 20 are extended via gear mechanisms shown generally at 22 and 23 out through their axial prosthesis channels 24, 25 into the adjacent vertebral bodies 14, 16 to secure prosthesis 12 therebetween.

Gear mechanisms 22, 23 include rack gear teeth 26 provided on the interior sides of each of the anchoring pins 18, 20. Rack gear teeth 26 communicate with wrench opening 28 when the pins are in their retracted position. Wrench opening 28 extends anteroposteriorly through prosthesis 12 to posterior wrench abutment plate 30. When it is desired to advance the pins, a pinion wrench 32 is inserted anteriorly into wrench opening 28, as best illustrated in FIG. 7. Referring to FIGS. 5 and 6, pinion wrench shown generally at 32 includes a cylindrical gear head 34 having protruding gear teeth, a gear shaft 35 secured to gear head 34 and a handle 36 perpendicularly attached to the outermost end of shaft 35. Wrench 32 is held by handle 36 and gear head 34 inserted into wrench opening 28 until it is in its further inserted position and in engagement with rack gear teeth 26 of the posterior pair 18 of oppositely disposed pins, as best shown in FIG. 5. Then wrench 32 is rotated via handle 36 until the pins are fully extended as shown in FIG. 4. Wrench 32 is then removed slightly out through wrench opening 28 until gear head 34 is in engagement with the anterior pair 20 of oppositely disposed pins as best shown in FIG. 6. Handle 36 is turned in the opposite direction and anterior pins 20 are advanced in their channels 25 from their retracted position to their fully extended position similar to the motion of the posterior pins but in opposite directions. It is also within the scope of the present invention to extend the anterior anchoring pins before the posterior anchoring pins. Anchoring pins 18, 20 thereby fix prosthesis 12 in place between neighboring vertebral bodies 14 and 16 and thus stabilize the vertebral bodies one to the other.

In lieu of the gearing arrangements of FIGS. 5 and 6, an alternative gear mechanism can be used as shown generally at 38 in FIG. 8. Referring thereto, it is seen that two pinion gears 40, 42 are fitted into wrench hole 28 with a cylindrical spacer 44 between them within prosthesis 12. Each pinion gear has a square opening 46, 48, respectively, extending therethrough. A wrench similar to pinion wrench 32 but having a square gear head 50 is then temporarily inserted into posterior gear head opening 46. The sides of square gear head 50 engage the surfaces of the square opening 46. When the wrench is turned gear head 40 turns and the posterior pins 18 are extended similar to the first embodiment. After the posterior pins 18 have been advanced to their fully extended position, wrench 32 is pulled slightly out of wrench opening 28 until wrench gear head 50 is in engagement with the anterior pinion gear 42. Wrench 32 is then twisted in the other direction via handle 36 and the anterior pair of pins 20 are advanced to their fully extended position. Wrench 32 is then completely removed from prosthesis 12 out through wrench opening 28 and pinion gears 40, 42 remain within prosthesis 12.

Referring to FIGS. 3 and 4 it is seen that each of the anchoring pins 18, 20 has associated with it two spring-loaded detent pins 52, 54, which are screwed into the side openings 56 of prosthesis 12 and are in engagement with the side of anchoring pins as shown in FIG. 3. Detent pins 52, 54 bias the anchoring pins towards wrench opening 28 and against pinion gear head 34 when inserted providing an interlocking between the gear rack teeth. Detent pins 18, 20 also have a track 58 extending longitudinally on their outside surface opposite the tooth gear 26 and anchoring pins 52, 54 ride in tracks 58 as the pins are extended into the adjacent vertebral bodies. When the pins are in their fully extended position, detent pins 52, 54 then engage into a pair of spaced holes 60, 62 in anchoring pins 18, 20 thereby locking the pins in place and thus preventing their movement back into prosthesis 12. Hole 60 which is nearest the pointed pin tip is provided with a chamfered shoulder 64, which allows the innermost retaining pin 52 to ride freely up the shoulder and to continue riding until it is engaged and held in hole 62.

Prior to extending anchoring pins 18, 20 but after prosthesis 12 has been positioned between the vertebral bodies 14, 16, a biocompatible metal retaining plate 66 which overlaps the two abutting vertebral bodies is attached to the bodies 14, 16 as well as to the prosthesis 12. Plate 66 secures prosthesis 12 in place and prevents its posterior migration. Plate 66 is secured via machine screws 68 screwed into aligned holes in the plate and the prosthesis, as best shown in FIG. 7. Plate 66 is directly fastened to the bony structure of the vertebral bodies, as shown in FIG. 2, by bone screws 69 through holes in the overlapping ends of plate 66.

Figure 9:
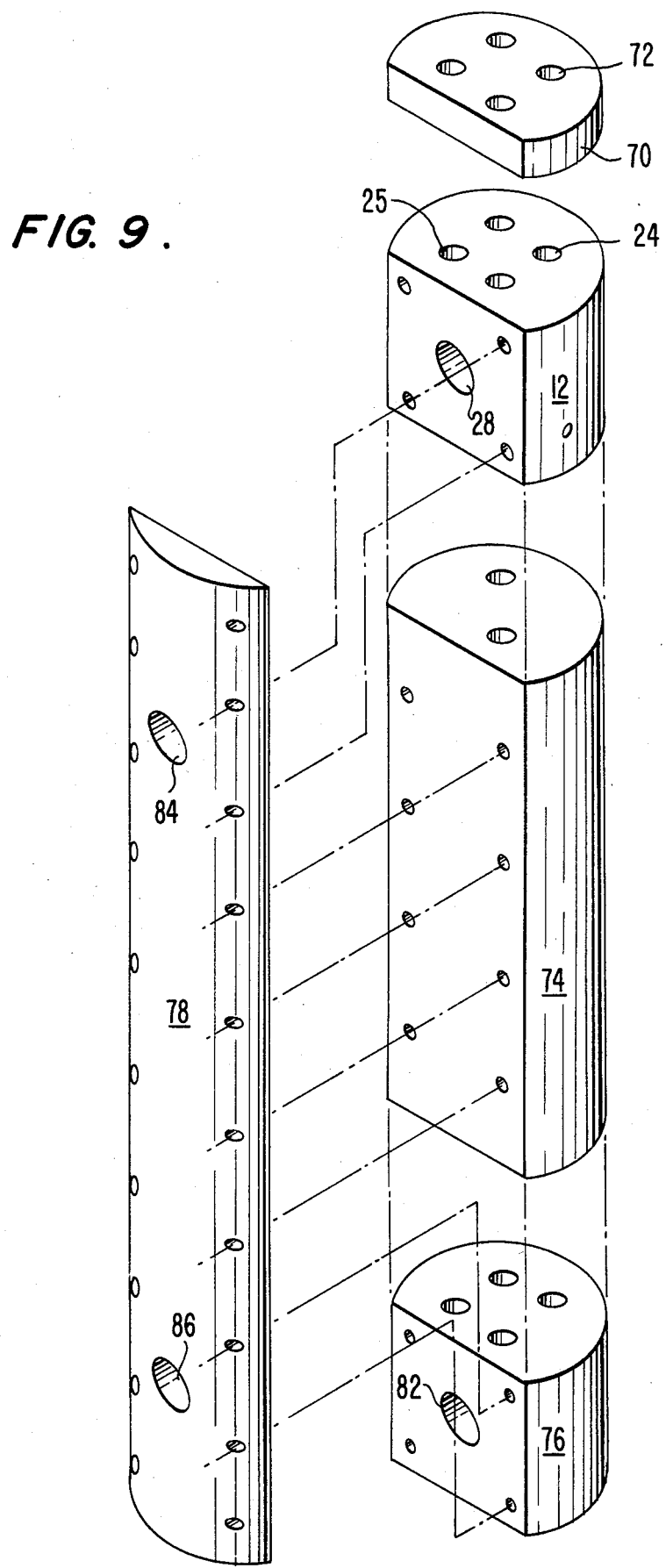
FIG. 9 is an exploded perspective view of a spine stabilization device according to the present invention that incorporates spacers for replacing multiple consecutive vertebral bodies.

The present invention also provides that spine stabilization device 10 can be elongated to accommodate greater dimensions between separated vertebral bodies. This can be done in one of two ways or a combination thereof, as illustrated in FIG. 9. First, when the additional elongated distance needed is not great a spacer member 70 having the same general cross-sectional configuration as prosthesis 12 can be positioned between the end surface of the prosthesis 12 and the first vertebral body 14. To provide rigidity spacer member 70 can be first screwed to prosthesis 12. Its holes 72 are aligned with channels 24, 25 of prosthesis 12. A longer retaining plate is secured in place and pins 18, 20 are extended via the gear mechanism as previously described. The pins will freely pass through holes 72 of spacer member 70. Spacer member 70 can be provided in a variety of different widths to accommodate different spinal configurations with each spacer measuring various fractions of a vertebral body and/or vertebral interspace. Second, in addition to or in lieu of spacer member 70, a longer prosthesis spacer 74 can be used for spanning multiple vertebral bodies, as shown in FIG. 9. For this embodiment a second generally identical prosthesis 76 is provided and prosthesis spacer 74 is placed between two vertebral body prosthesis 12, 76. Prosthesis 12, 76 and the spacer 74 are then connected with a connecting plate 78 as shown in FIG. 9 and secured thereto by machine screws 68 passing through aligned openings with the wrench openings 28 and 82 in connecting plate 78 being aligned with the openings 84, 86 in the two vertebral body prosthesis. Then using the stabilizing pin setting wrench 32 the anchoring pins of prosthesis 12 are advanced until they extend into the first vertebral body 14 on the one side and on the other side into prosthesis spacer 74. Similarly the anchoring pins (not shown) in the second vertebral body prosthesis 76 are advanced until they extend into the second vertebral body 16 at one end and into the prosthesis spacer 74 at the other end. The ends of connecting plate 78 that overlap abutting vertebral bodies 14, 16 are fixed to those vertebral bodies by means of bone screws 69 in the fashion depicted in FIGS. 2 and 7.

From the foregoing detailed description it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

I claim:
1. A spine stabilization device comprising:
    a vertebral body prosthesis adapted to be positioned between first and second separated vertebral bodies,
    said prosthesis having a prosthesis first end and an opposite prosthesis second end,
    a first anchoring pin extendible relative to said prosthesis and out of said prosthesis first end,
    a second anchoring pin extendible relative to said prosthesis and out of said prosthesis second end, and
    a rack gear means for extending said first anchoring pin out of said prosthesis first end and driving it into said first vertebral body to secure said prosthesis to said first vertebral body, when said prosthesis is positioned between said first and second vertebral bodies, and for extending said second anchoring pin out of said prosthesis second end towards said second vertebral body.
2. The device of claim 1 including,
    said rack gear means being positioned within said prosthesis between said prosthesis first and second ends.
3. The device of claim 1 including,
    said first anchoring pin including a gear-toothed surface portion, and
    said rack gear means being operatively engageable with said gear-toothed surface portion.
4. The device of claim 3 including,
    said rack gear means including a rotatable gear member engageable with said gear-toothed surface portion and, when rotated, causing said first anchoring pin to extend out of said prothesis.
5. The device of claim 4 including,
    said rack gear means including a shaft affixed to said rotatable gear member and extending out from said prosthesis and a handle at the outer end of said shaft adapted to be grasped and rotated.
6. The device of claim 4 including,
    said rack gear means including said rotatable gear member being mounted in said prosthesis and engaging said gear-toothed portion, and a handle insertable into said prosthesis to engage said rotatable gear member such that said rotatable gear member is turned by turning said handle.
7. The device of claim 1 including,
    said rack gear means extending said first and second anchoring pins simultaneously relative to said prosthesis.
8. The device of claim 1 including,
    a guide means connected to said prosthesis for guiding said first anchoring pin as said rack gear means extends said first anchoring pin out of said prosthesis.
9. The device of claim 8 including,
    said prosthesis including a side wall, and
    said guide means including a spring-loaded detent pin attached to said side wall and biasing against said first anchoring pin.
10. The device of claim 9 including,
    said first anchoring pin having a stop groove in which said detent pin engages when said first anchoring pin is in its fully extended position relative to said prosthesis for securing said first anchoring pin in said fully extended position.
11. The device of claim 9 including,
    said detent pin biasing said first anchoring pin against and in engagement with said rack gear means.
12. The device of claim 9 including,
    said first anchoring pin including a groove having a rear chamfered shoulder sloping away from the outer end of said first anchoring pin, and
    said detent pin engaging in said groove when said first anchoring pin is in its retracted position relative to said prosthesis.
13. The device of claim 9 including,
    said first anchoring pin having a longitudinal guide track along which said detent pin moves.
14. The device of claim 1 including,
    said first anchoring pin having its inner pin end positioned entirely within said prosthesis.
15. The device of claim 1 including,
    a third anchoring pin extendible relative to said prosthesis and out of said prosthesis first end and into said first vertebral body.
16. The device of claim 15 including,
    said third anchoring pin having its inner pin end positioned entirely within said prosthesis.
17. The device of claim 15 including,
    said rack gear means being engageable with said third anchoring pin.
18. The device of claim 15 including,
    a fourth anchoring pin extendible relative to said prosthesis and out of said prosthesis second end.

19. The device of claim 18 including,
said rack gear means extending said third and fourth anchoring pins simultaneously and in opposite directions relative to said prosthesis.

20. The device of claim 19 including,
said rack gear means extending said first and second anchoring pins simultaneously and in opposite directions relative to said prosthesis.

21. The device of claim 20 including,
said rack gear means extending said first and second anchoring pins after extending said third and fourth anchoring pins.

22. The device of claim 1 including,
said rack gear means extending said second anchoring pin so that it is driven into said second vertebral body to secure said prosthesis to said second vertebral body.

23. The device of claim 1 including,
an elongated vertebral spacer positionable between said prosthesis and said second vertebral body,
said rack gear means extending said second anchoring pin into said vertebral spacer and securing said vertebral spacer to said prosthesis, and
a securing means for securing said vertebral spacer to said second vertebral body.

24. The device of claim 23 including,
said securing means including a second prosthesis and an anchoring pin means extendible out from said second prosthesis and into said second vertebral body.

25. The device of claim 24 including,
said anchoring pin means securing said vertebral spacer to said second prosthesis.

26. The device of claim 24 including,
a retaining plate positioned adjacent and secured to said prosthesis, said vertebral spacer and said second prosthesis.

27. The device of claim 26 including,
an attaching means for attaching said retaining plate directly to the anterior sides of said prosthesis, said vertebral spacer and said second prosthesis.

28. The device of claim 1 including,
said prosthesis being interposed between said first and second vertebral bodies after distracting said vertebral bodies by temporarily attaching a distraction device.

29. The device of claim 1 including,
said prosthesis having an anterior face, and
an elongated anterior plate secured directly to said anterior face and to said first and second vertebral bodies, when said prosthesis is positioned between said first and second vertebral bodies.

30. The device of claim 29 including,
a securing means for securing said plate to said anterior face after said rack gear means has extended said first anchoring pin into said first vertebral body.

31. The device of claim 29 including,
at least one bone screw passing through said plate and into said first and second vertebral bodies for securing said plate thereto.

32. The device of claim 1 including,
said prosthesis first end including a first end opening through which said first anchoring pin passes,
said prosthesis second end including a second end opening through which said second anchoring pin passes, and
said prosthesis including a side wall secured to said prosthesis first and second ends and immovably fixing them in spaced relation.

33. The device of claim 1 including,
said rack gear means including a gear-toothed member connected to said first anchoring pin and a rotatable gear member engageable with said gear-toothed member and, when rotated, causing said first anchoring pin to extend out of said prosthesis.

34. The device of claim 33 including,
a handle positionable to pass through said prosthesis and engage said rotatable gear member so that when said handle is turned said rotatable gear member is rotated.

35. The device of claim 1 including,
said prosthesis including a solid posterior wall connected to and extending between said first and second ends.

36. The device of claim 1 including,
said rack gear means including a gear-carrying key.

37. The device of claim 1 including,
said rack gear means including a hexagonal wrench.

38. The device of claim 1 including,
a locking means connected to said prosthesis for locking said first and second anchoring pins in position after said rack gear means has forced said first anchoring pin deeply into said first vertebral body and extended said second anchoring pin out of said prosthesis.

39. The device of claim 1 including,
said first and second anchoring pins being connected to and being positioned generally entirely inside of said prosthesis before being extended by said rack gear means.

40. A spine stabilization device comprising:
a vertebral body prosthesis adapted to be positioned between first and second separated vertebral bodies,
said prosthesis having a prosthesis first end and an opposite prosthesis second end,
a first anchoring pin extendible relative to said prosthesis, and out of said prosthesis first end
said first achoring pin including a gear-toothed surface portion
a second anchoring pin extendible relative to said prosthesis, and out of said prosthesis second end
said second anchoring pin including a second pin gear-toothed surface portion
a rotatable gear member positionable within said prosthesis and engageable with said gear toothed surface portion and with said second pin gear toothed surface portion, and
a handle engageable with said rotatable gear member and when turned causing said first anchoring pin to extend further out of said prosthesis first end and into said first vertebral body to secure said prosthesis thereto and causing said second anchoring pin to extend further out of said prosthesis second end.

41. A method for stabilizing a spine having separated but neighboring first and second vertebral bodies comprising the steps of:
further separating apart with a distraction device said first and second vertebral bodies,
thereafter, positioning between said first and second vertebral bodies a vertebral body prosthesis containing a pair of oppositely disposed anchoring pins, and thereafter, advancing out of said prosthesis via a rack gear mechanism said anchoring pins so that the one of said anchoring pins penetrates a distance into said first vertebral body and secures said prosthesis thereto, and the other extends out of said prosthesis towards said second vertebral body.

42. The method of claim 41 including,
after said positioning, securing a retaining plate to said prosthesis.

43. The method of claim 42 including,
said securing including securing said retaining plate to the anterior side of said prosthesis.

44. The method of claim 42 including,
said securing including securing said retaining plate to said first and second vertebral bodies as well.

45. The method of claim 41 including,
said separating step being performed when the vertebral body is diseased.

46. The method of claim 41 including,
said positioning including anteriorly positioning said prosthesis.

47. The method of claim 41 including,
said advancing including advancing out of said prosthesis the other one of said anchoring pins so that it penetrates a distance into said second vertebral body and secures said prosthesis thereto.

48. The method of claim 41 including,
said positioning including positioning said prosthesis adjacent said first vertebral body.

49. The method of claim 41 including,
after said advancing, locking said anchoring pins to said prosthesis in their advanced positions.

* * * * *